US006074880A

United States Patent [19]

Sutton et al.

[11] Patent Number: 6,074,880

[45] Date of Patent: Jun. 13, 2000

[54] SAMPLE ANALYTE CONTAINING SOLUTION FRACTION COLLECTION SYSTEM, AND METHOD OF USE

[75] Inventors: John E. Sutton; Donn H. Vanden Bosch, both of Bellevue, Nebr.

[73] Assignee: Transgenomic, Inc., San Jose, Calif.

[21] Appl. No.: 09/143,456

[22] Filed: Aug. 28, 1998

[51] Int. Cl.[7] .......... G01N 1/14

[52] U.S. Cl. .......... 436/52; 436/161; 436/174; 436/180; 422/63; 422/70; 422/81; 422/100; 422/102; 73/61.43; 73/61.52; 73/61.59; 220/630; 220/637

[58] Field of Search .......... 436/43, 52, 53, 436/161, 174, 180; 422/63, 70, 81, 100, 103; 73/61.43, 61.52, 61.59; 222/630, 637

[56] References Cited

U.S. PATENT DOCUMENTS

| | | | |
|---|---|---|---|
| 3,746,217 | 7/1973 | Hanset et al. | 222/194 |
| 4,066,409 | 1/1978 | Fine | 422/70 |
| 4,491,011 | 1/1985 | Nordmeyer et al. | 73/61.1 C |
| 4,497,199 | 2/1985 | Matson | 73/63.1 C |
| 5,003,830 | 4/1991 | Spencer | 73/863.83 |
| 5,259,254 | 11/1993 | Zhu et al. | 73/864.81 |
| 5,310,463 | 5/1994 | Dadoo et al. | 204/180.1 |
| 5,389,221 | 2/1995 | Jorgenson et al. | 204/299 R |
| 5,391,499 | 2/1995 | Karkantis et al. | 436/180 |
| 5,448,062 | 9/1995 | Cooks et al. | 250/288 |
| 5,520,817 | 5/1996 | Anahara | 210/656 |
| 5,565,622 | 10/1996 | Murphy | 73/61.55 |
| 5,585,236 | 12/1996 | Bonn et al. | 435/5 |
| 5,593,564 | 1/1997 | Templin et al. | 204/451 |
| 5,872,010 | 2/1999 | Karger et al. | 436/173 |
| 5,898,175 | 4/1999 | Hirabayashi et al. | 250/288 |
| 5,917,184 | 6/1999 | Carson et al. | 250/288 |
| 5,976,336 | 11/1999 | Dubrow et al. | 204/453 |

*Primary Examiner*—Long V. Le
*Attorney, Agent, or Firm*—William B. Walker

[57] ABSTRACT

Disclosed is a system and method which allows user controlled formation, and ejection of droplets of sample analyte containing solutions, thereby enabling precise user directed fractionalization and distributed collection of sample analytes.

8 Claims, 2 Drawing Sheets

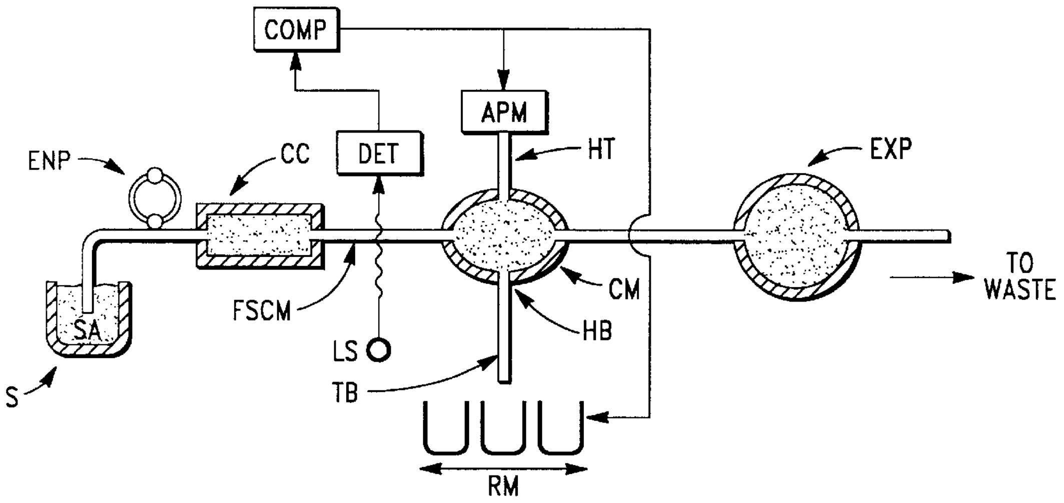
FIG.−1
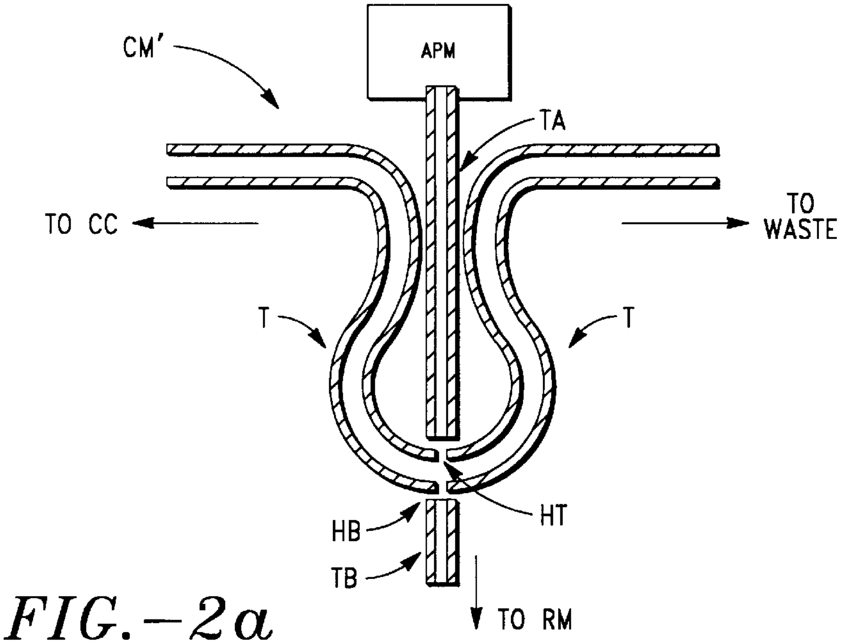
FIG.−2a
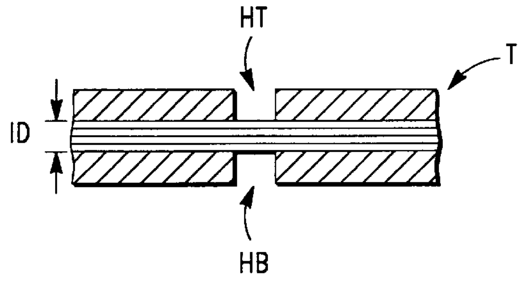
FIG.−2b

SAMPLE ANALYTE CONTAINING SOLUTION FRACTION COLLECTION SYSTEM, AND METHOD OF USE

TECHNICAL AREA

The present invention relates to fraction collection of sample analyte containing solutions. More particularly the present invention is a system and method which allows user controlled formation, and ejection, of small volume droplets of sample analyte containing solutions, thereby enabling precise user directed fractionalization and distributed collection of sample analyte(s).

BACKGROUND

As is well known to practitioners of, for instance, High Pressure Liquid Chromatography (HPLC), (also known as High Performance Liquid Chromatography), it is often necessary to coordinate fractionalization of sample analyte (s) containing solutions with the positioning of collection means, so that fractional collection of separate analyte components in said sample analyte(s) containing solution can be separated and individually collected.

Briefly, High Pressure/Performance Liquid Chromatography (HPLC), is a method by which a solution containing multiple sample analytes is caused to flow through a Chromatography Column which is packed with a material that demonstrates different affinities for different of present sample analytes. The beneficial result is that various sample analytes present in said solution, exit the Chromatography Column at sequentially progressive, different times. (It is noted that the Chromatography Column is often referred to as the Stationary Phase and the Eluent as the Mobile Phase).

It is to be understood that the time at which a specific sample analyte in a solution exits a Chromatography Column is determined by properties of the packing material therein, the strength and effectiveness of the mobile phase, the sample analyte present, the flow rate of the sample solution, and other factors such as temperature and pressure in the Chromatography Column etc. And, it is to be understood that if it is desired to fractionate a solution exiting a Chromatography Column, and separately distribute different analytes present therein into different receiving means, then it is necessary to coordinate the fractionalization of the solution and the positioning of said receiving means.

There are various approaches to accomplishing fractionalization of solutions. One approach requires only that a sequence of receiving means be positioned to receive soultion exiting a Chromatography Column, with some schedule of time periods determining when a receiving means positioned so as to receive solution is moved and another receiving means so placed. After such a run, the various receiving means are tested to determine which contain the desired sample analytes, and the contents of other receiving means are discarded.

Another approach requires that solution exiting a Chromatography Column be directed into a waste station, and when desired a receiving means is positioned to receive a sample. This is usually accomplished utilizing a rotary tray. It is noted that rotary trays are limited in how many receiving means can be utilized, and precludes use of "micro-plates".

Valves are, at times, employed in procedures to control the fractionalization process of a solution, but dripping between sample collection, and the occurrence of dead-volumes can present as problems to successful practice of said procedures.

Problems facing a user when practicing said known approaches to accomplishing fractionalization of solutions include a less than definite control as to when a sample of a solution exiting a Chromatography Column is collected, and little control over the volume of samples collected.

It is also noted that an absorbance based detector can be used to determine when a sample analyte is present in and near the end of a chromatography column, and a signal from said detector which can be based upon a change in slope of a detected signal or based upon the reaching of a threshold value, can be used to control when a sample fraction is to be collected.

With an eye toward the present invention, a search of Patents was performed, with the most significant result being that very few Patents were identified.

A Patent to Hanset. et al., U.S. Pat. No. 3,746,217 is perhaps the closest Patent which found, as it describes a metering system for application in disbursing accurate amounts of catalyst. Said 217 Patent system incorporates a piston rod which in use serves to position a chamber so that it can first receive an amount of catalyst, and then disburse said received amount of catalyst. Said disbursement is mediated by an air blast.

A Patent to Bonn et al., U.S. Pat. No. 5,585,236 is also disclosed, and incorporated herein by reference, as it describes a particulary relevant chromatography column for spearating single and double stranded nucleic acids, which can be utilized with the present invention.

Patents also identified by the Searcher, but which are not considered to be relevant and which are disclosed herein only because the inventors are aware thereof, are U.S. Pat. No. 5,003,830 to Spencer, U.S. Pat. No. 5,448,062 to Cooks et al. and U.S. Pat. No. 5,259,254 to Zhu et al.

A system and method which would provide a user thereof definite control as to when a fractionated sample of a solution exiting a chromatography column is obtained, and provide a user control over the size of said fractionated sample obtained, would provide presently unavailable utility.

DISCLOSURE OF THE INVENTION

In one respect, the present invention is system for enabling ejection of a drop of sample analyte containing solution from a contained flow stream thereof. Said system comprises a source of sample analyte containing solution and a sample analyte containing flow stream containing means for receiving sample analyte containing solution, in combination with a chamber means for receiving sample analyte containing solution from said sample analyte containing flow stream containing means. Said chamber means further has an opening therein for entering gas and an opening therein from which a drop of sample analyte containing solution can be ejected. In addition said system comprises entry pumping means for causing sample analyte containing solution contained in said source thereof to enter said sample analyte containing flow stream containing means for receiving sample analyte containing solution, in combination with a chamber means for receiving sample analyte containing solution from said sample analyte containing flow stream containing means. Said system also typically comprises exit pumping means for promoting or blocking the exit of sample analyte containing solution caused to be present in said chamber means therefrom, and a means for providing a puff of gas into said opening for entering gas in said chamber means.

In use sample analyte containing solution from said source thereof is caused, by said entry pumping means, to enter said sample analyte containing flow stream containing means and flow into said chamber means, with exit of said sample analyte containing solution from said chamber means is promoted, or blocked, by said exit pumping means. While said sample analyte containing solution is present in said chamber means, a drop thereof can be caused to be ejected from said opening therein from which a drop of sample analyte containing solution can be ejected, by entry of a puff of gas from said means for providing a puff of gas to said opening in said chamber means for entering gas. Optionally, said exit pumping means, when present, can be utilized to block the exit of sample analyte containing solution caused to be present in said chamber means, when said puff of gas is entered to said chamber means.

It is noted that a non-limiting presently preferred "chamber means" is teflon tubing with an inner diameter of five-thousandths (5⁄1000) inch and an outer diameter of sixty-three-thousandths (63⁄1000) inch, through the walls of which has been drilled a hole, said hole being drilled essentially along an inner diameter of said teflon tubing, when said teflon tubing is held at liquid nitrogen temperatures. The diameter of the drilled hole is typically a ten-thousandths (10⁄1000) inch. The optimum tube inner diameter and drilled hole diameter, will however, vary with flow rate.

In another respect, the present invention is a method of ejecting a drop of sample analyte containing solution from a contained flow stream thereof, comprising the steps of:

1. providing a system for ejecting a drop of sample analyte containing solution from a flow stream thereof as just described;

2. by application of said entry pumping means causing sample analyte containing solution from said source thereof, to enter said sample analyte containing flow stream containing means and into said chamber means;

3. entering a puff of gas, from said means for providing a puff of gas to said opening in said chamber means for entering gas, into said opening for entering gas in said chamber means, while optionally causing a present exit pumping means to block the exit of sample analyte containing solution caused to be present in said chamber means therefrom;

to the end that a drop of sample analyte containing solution exits from said chamber means via said opening therein from which a drop of sample analyte containing solution can be ejected.

Said method of ejecting a drop of sample analyte containing solution from a contained flow stream thereof can further comprise the step of causing said exit pumping means to block the exit of sample analyte containing solution caused to be present in said chamber means, therefrom, simultaneous with entering a puff of gas from said means for providing a puff of gas to said opening in said chamber means for entering gas.

Said method of ejecting a drop of sample analyte containing solution from a contained flow stream thereof can also further comprise the step of providing and positioning a receiving means under said opening in said chamber means from which a drop of sample analyte containing solution can be ejected, such that said ejected drop of sample analyte containing solution is entered into said receiving means.

A preferred present invention system for ejecting a drop of sample analyte containing solution from a contained flow stream thereof comprises a source of sample analyte containing solution; a chromatography column; an entry pumping means for causing sample analyte containing solution contained in said source thereof to enter, pass through and exit said chromatography column. Said preferred system further comprises a sample analyte containing flow stream containing means for receiving sample analyte containing solution exiting said chromatography column in combination with a chamber means for receiving sample analyte containing solution from said sample analyte containing flow stream containing means. Said chamber means has an opening therein for entering gas and an opening therein from which a drop of sample analyte containing solution can be ejected. Said preferred system further has as exit pumping means for promoting or blocking the exit of sample analyte containing solution caused to be present in said chamber means therefrom, and a means for providing a puff of gas into said opening for entering gas in said chamber means.

In use, sample analyte containing solution from said source thereof is caused, by said entry pumping means, to enter said chromatography column, flow therethrough, exit therefrom, enter said sample analyte containing flow stream containing means and into said chamber means, with exit of said sample analyte containing solution from said chamber means is promoted, or blocked, by said exit pumping means. While said sample analyte containing solution is present in said chamber means, a drop thereof can be caused to be ejected from said opening therein from which a drop of sample analyte containing solution can be ejected, by entry of a puff of gas from said means for providing a puff of gas to said opening in said chamber means for entering gas. Optionally, said exit pumping means can be utilized to block the exit of sample analyte containing solution caused to be present in said chamber means, when said puff of gas is entered to said chamber means.

It is again noted that a non-limiting presently preferred "chamber means" is teflon tubing with an inner diameter of five-thousandths (5⁄1000) inch, and an outer diameter of sixty-three-thousandths (63⁄1000) inch, through the walls of which has been drilled a hole, said hole being drilled essentially along an inner diameter of said teflon tubing, when said teflon tubing is held at liquid nitrogen temperatures. The diameter of the drilled hole is typically ten-thousandths (10⁄1000). In practice said hole tubing and drilled hole diameters are optimally set based upon sample analyte containing solvent type and flow rate etc.

A present invention method of ejecting a drop of sample analyte containing solution from a contained flow stream thereof, can then comprise the steps of:

1. providing a system for ejecting a drop of sample analyte containing solution from a flow stream thereof as just described;

2. by application of said entry pumping means causing sample analyte containing solution from said source thereof, to enter said chromatography column, flow therethrough, exit therefrom, enter said sample analyte containing flow stream containing means and into said chamber means;

3. entering a puff of gas, from said means for providing a puff of gas to said opening in said chamber means for entering gas, into said opening for entering gas in said chamber means, while optionally causing said exit pumping means to block the exit of sample analyte containing solution caused to be present in said chamber means therefrom;

to the end that a drop of sample analyte containing solution exits from said chamber means via said opening therein from which a drop of sample analyte containing solution can be ejected.

Said method of ejecting a drop of sample analyte containing solution from a contained flow stream thereof can further comprise the step of causing said exit pumping means to block the exit of sample analyte containing solution caused to be present in said chamber means, therefrom, simultaneous with entering a puff of gas from said means for providing a puff of gas to said opening in said chamber means for entering gas.

Said method of ejecting a drop of sample analyte containing solution from a contained flow stream thereof can also further comprise the step of providing and positioning a receiving means under said opening in said chamber means from which a drop of sample analyte containing solution can be ejected, such that said ejected drop of sample analyte containing solution is entered into said receiving means.

Another more general recitation of the method bf ejecting a drop of sample analyte containing solution from a contained flow stream thereof comprises the steps of:

a. providing a contained sample analyte containing flow stream;

b. causing said contained sample analyte containing flow stream to pass into a chamber means thereof, said chamber means having an opening therein for entering gas and an opening therein from which a drop of sample analyte containing solution can be ejected;

c. causing a puff of gas to enter said opening for entering gas in said chamber means;

such that a drop of sample analyte containing solution is ejected from the opening.

Said method of ejecting a drop of sample analyte containing solution from a contained flow stream thereof can further comprise the step of providing and positioning a receiving means under said opening in said chamber means from which a drop of sample analyte containing solution can be ejected, such that said ejected drop of sample analyte containing solution is entered into said receiving means.

Said more general recitation of a present invention method of ejecting a drop of sample analyte containing solution from a contained flow stream thereof can, where a chromatography column is present, comprise the steps of:

a. providing a source of sample analyte containing solution;

b. providing a chromatography column;

c. causing a flow of sample analyte containing solution from said source thereof to enter said chromatography column such said sample analyte containing solution flows through said chromatography column and exits therefrom;

d. providing a sample analyte containing flow stream containing means and entering said flow of sample analyte containing solution exiting said chromatography column thereinto to form a contained sample analyte containing flow stream therein;

e. providing a chamber means having an opening therein for entering gas and an opening therein from which a drop of sample analyte containing solution can be ejected, and causing said contained sample analyte containing flow stream to pass into a chamber means from said sample analyte containing flow stream containing means;

f. causing a puff of gas to enter said opening for entering gas in said chamber means;

such that a drop of sample analyte containing solution is ejected from the opening therein from which a drop of sample analyte containing solution can be ejected.

Again said present invention method of ejecting a drop of sample analyte containing solution from a contained flow stream thereof can further comprises the step of providing and positioning a receiving means under said under said opening in said chamber means from which a drop of sample analyte containing solution can be ejected, such that said ejected drop of sample analyte containing solution is entered into said receiving means.

Typical practice is to control the various system operations described, (eg. operation of said entry pumping means and said exit pumping means and said means for providing a puff of gas into said opening for entering gas in said chamber means, and positioning said receiving means), from a computer system.

In any foregoing embodiment and/or method of use, it is to be understood that the "entry pumping means" is a peristaltic pump and the "exit pumping means" can be a peristaltic pump, but experimental work has shown that a vacuum pump with an in-line valve means provides superior operating characteristics.

Also in any foregoing embodiment and/or method of use, it is to be understood that the causing of a puff of gas to enter said opening for entering gas in said chamber means can be caused by a signal from a detector system, (optionally time delayed), which monitors the presence of an analyte in the chamber means. Such a detector system can be, but is not necessarily, an absorbtion-type electromagnetic beam intensity monitoring system which causes a beam of electromagnetic radiation to pass through sample analyte containing solution present in said sample analyte containing flow stream containing means, just prior to the chamber means.

The present invention will be better understood by reference to the Detailed Description Section of this Disclosure, in conjunction with the Drawings.

SUMMARY OF THE INVENTION

It is therefore a purpose of the present invention to provide a system for enabling ejection of a drop of sample analyte containing solution from a "chamber means" which receives a contained flow stream thereof.

It is another purpose of the present invention to describe a preferred "chamber means" from which a drop of sample analyte containing solution can be ejected which comprises a teflon tube through the walls of which has been drilled a hole essentially along an inner diameter of said teflon tubing.

It is yet another purpose of the present invention to describe a method of ejecting a drop of sample analyte containing solution from a contained flow stream thereof.

It is yet another purpose of the present invention to describe application in a system which includes a chromatography column.

BRIEF DESCRIPTION OF THE DRAWINGS

FIG. 1 shows a preferred present invention system for ejecting a drop of sample analyte containing solution from a contained flow stream thereof.

FIG. 2*a* shows that a preferred embodiment of a chamber means as shown in FIG. 1.

FIG. 2*b* better demonstrates a chamber means comprising a teflon tube with an inner diameter through the walls of which has been drilled a hole, defined at top and bottom.

DETAILED DESCRIPTION

Figure 3:
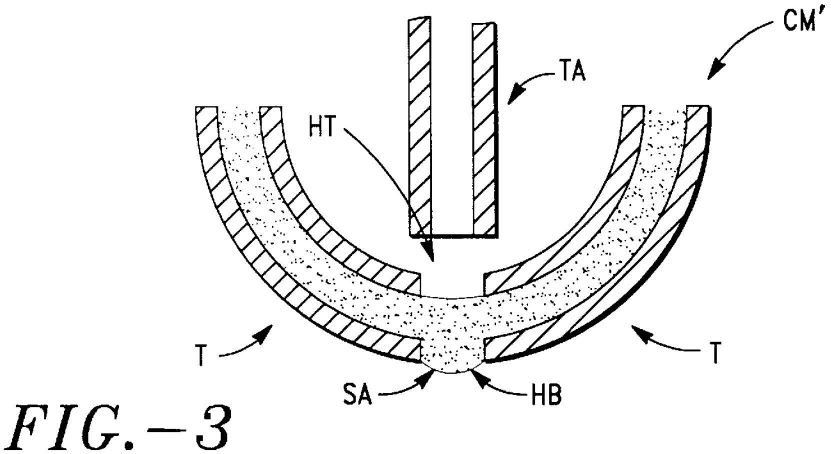
FIG. 3 shows that sample analyte containing solution caused to be present inside teflon tubing (T) does not exit through said opening therein (HB) from which a drop (D) of sample analyte containing solution can be ejected as it flows through said teflon tube (T).

Turning now to FIG. 1, there is shown a preferred present invention system for ejecting a drop of sample analyte containing solution from a contained flow stream thereof. Shown are a source (S) of sample analyte (SA) containing solution; a chromatography column (CC); entry pumping means (ENP) for causing sample analyte (SA) containing solution contained in said source (S) thereof to enter, pass through and exit said chromatography column (CC); and a sample analyte (SA) containing flow stream containing means (FSCM) for receiving sample analyte (SA) containing solution exiting said chromatography column (CC) in combination with a chamber means (CM) for receiving sample analyte (SA) containing solution from said sample analyte containing flow stream containing means (FSCM). A Light Source (LS) and Detector (DET) are shown oriented such that an electromagnetic beam is caused to pass through sample analyte in the flow stream containing means (FSCM). In use, a signal from the Detector (DET), can be used to trigger the means to operating a means for providing a puff of gas (APM) and for properly positioned receiving means (RM), and such can be coordinated by a Computer (COMP) system. Said chamber means (CM) is shown to have an opening therein for entering gas (HT) and an opening therein from which a drop of sample analyte containing solution can be ejected (HB). Also shown is an exit pumping means (EXP) for promoting or blocking the exit of sample analyte (SA) containing solution caused to be present in said chamber means (CM) therefrom; and said means for providing a puff of gas (APM) into said opening for entering gas (HT) in said chamber means (CM). Note that the exit pumping means (EXP) can be a peristaltic pump such as diagramatically shown for the entry pumping means (ENT), or preferably said exit pumping means (EXP) is a vacuum pump.

In use, sample analyte (SA) containing solution from said source (S) thereof is caused, by said entry pumping means (ENP), to enter said chromatography column (CC), flow therethrough, exit therefrom, enter said sample analyte containing flow stream containing means (FSCM) and into said chamber means (CM), with exit of said sample analyte (SA) containing solution from said chamber means (CM) is promoted, or blocked, by said exit pumping means (EXP). While said sample analyte (SA) containing solution is present in said chamber means (CM), a drop, (see (D) in FIG. 4)), thereof can be caused to be ejected from said opening therein from which a drop of sample analyte containing solution can be ejected (MB), by entry of a puff of gas from said means for providing a puff of gas (APM) to said opening in said chamber means (CM) for entering gas (HT). Optionally, said exit pumping means (EXP) to block the exit of sample analyte (SA) containing solution caused to be present in said chamber means. (CM), therefrom.

Turning now to FIG. 2*a*, it is to be noted that a preferred, but not limiting, chamber means (CM) is teflon tubing (T) with an inner diameter of five-thousandths (5/1000) inch through the walls of which has been drilled a hole, defined at top and bottom by (HT) and (HB) respectively, said hole being drilled essentially along an inner diameter of said teflon tubing (T), when said teflon tubing (T) is held at liquid nitrogen temperatures. The diameter of the drilled hole is typically ten-thousandths (10/1000) inch. Also shown are tube (TA) through which a puff of gas can be entered to said opening in said chamber means (CM) for entering gas (HT), and a bottom tube (TB) through which a drop of sample analyte (SA) containing solution can exit in response thereto. FIG. 2*b* better demonstrates the teflon tubing (T) with an inner diameter (ID) through the walls of which has been drilled a hole, defined at top and bottom by (HT) and (HB) respectively.

Figure 4:
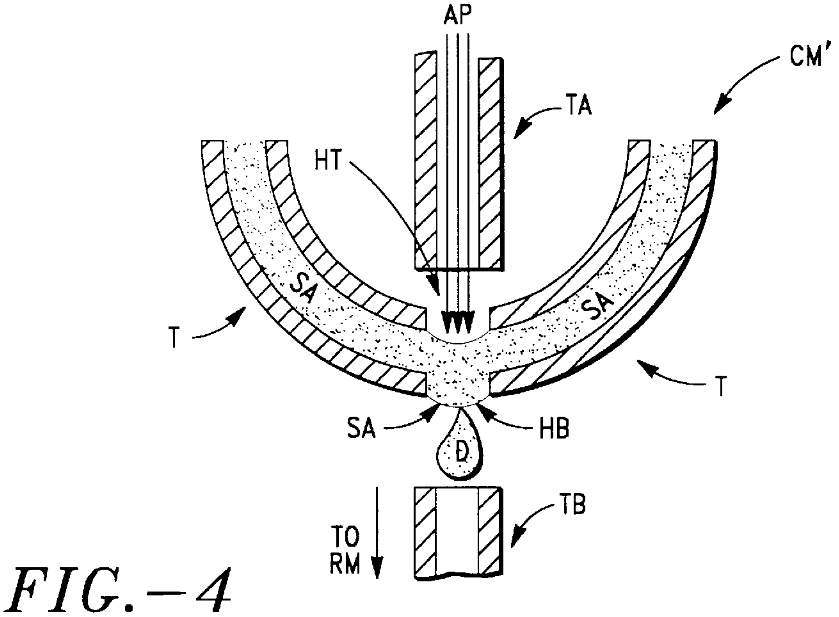
FIG. 4 demonstrates that when a puff of gas is entered via a tube (TA) in FIG. 3 and through said hole (HT), that a drop (D) of sample analyte (SA) containing solution is forced out of said opening in from which a drop of sample analyte containing solution can be ejected (HB), in said teflon tube (T).

FIG. 3 shows that sample analyte (SA) containing solution caused to be present inside teflon tubing (T) does not exit through said opening therein from which a drop of sample analyte containing solution can be ejected (HB) as it flows through said teflon tube (T). FIG. 4 demonstrates that when a puff of gas (AP) is entered via tube (TA) and through said hole (HT), that a drop (D) of sample analyte (SA) containing solution is forced out of said opening in from which a drop of sample analyte containing solution can be ejected (HB), in said teflon tube (T). Said drop (D) can then enter bottom tube (TB) and be directed into a properly positioned receiving means (RM).

Figure 5:
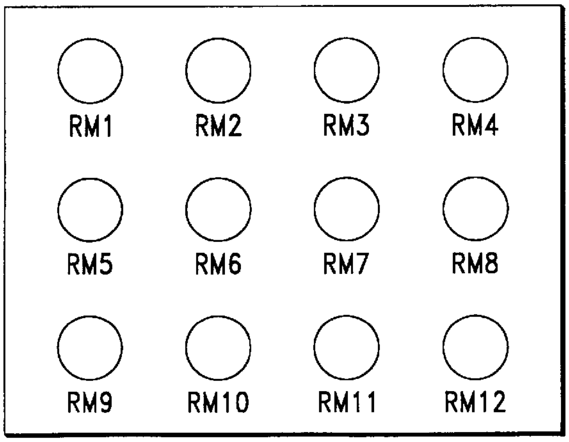
FIG. 5 demonstrates a receiving means comprising an array of a plurality of receiving means.

FIG. 5 demonstrates that receiving means can be an array of a plurality of receiving means. Said array can be mounted on a positioning means in application to the present invention, such that where an intended, specific, receiving means, (eg. RM1, RM2, RM3 . . . ), is positioned directly beneath a bottom tube (TB), (see FIG. 1), and a puff of gas is caused to be entered into said opening for entering gas (HT) in said chamber means (CM), by said means for providing a puff of gas (APM), a drop (D) of sample analyte (SA) containing solution is caused to be entered thereinto, via bottom tube (TB).

It is to be understood that while a primary use of the present invention is in systems which contain a High Pressure, (or alternatively "High Performance"), Chromatography Column (HPCC) as a source of sample analyte containing solution, any source of a solution which is to be fractionated, and which is caused to be present in chamber means (CM), can be utilized.

Having hereby disclosed the subject matter of the present invention, it should be obvious that many modifications, substitutions, and variations are possible in light thereof. It is therefore to be understood that the present invention can be practiced other than as specifically described, and should be limited in breadth and scope only by the claims.

We claim:

1. A system for ejecting a drop of sample analyte containing solution from a flow stream thereof comprising:

a. a source of sample analyte containing solution;

b. a chromatography column;

c. entry pumping means for causing sample analyte containing solution contained in said source thereof to enter, pass through and exit said chromatography column;

d. a sample analyte containing flow stream containing means for receiving sample analyte containing solution exiting said chromatography column; in combination with a chamber means for receiving sample analyte containing solution from said sample analyte containing flow stream containing means; said chamber means having an opening therein for entering gas and an opening therein from which a drop of sample analyte containing solution can be ejected;

e. exit pumping means for promoting or blocking the exit of sample analyte containing solution caused to be present in said chamber means therefrom; and f. a means for providing a puff of gas into said opening for entering gas in said chamber means;

such that in use sample analyte containing solution from said source thereof is caused, by said entry pumping means, to enter said chromatography column, flow therethrough, exit therefrom, enter said sample analyte containing flow stream containing means and into said chamber means, with exit of said sample analyte containing solution from said chamber means being promoted, or blocked, by said exit pumping means, and such that while said sample analyte containing solution is present in said chamber means, a drop thereof can be caused to be ejected from said opening therein from which a drop of sample analyte containing solution can be ejected, by entry of a puff of gas from said means for providing a puff of gas to said opening in said chamber means for entering gas, while optionally causing said exit pumping means to block the exit of sample analyte containing solution caused to be present in said chamber means, therefrom.

2. A method of ejecting a drop of sample analyte containing solution from a flow stream thereof, comprising the steps of:

1. providing a system for ejecting a drop of sample analyte containing solution from a flow stream thereof comprising:
   a. a source of sample analyte containing solution;
   b. a chromatography column;
   c. entry pumping means for causing sample analyte containing solution contained in said source thereof to enter, pass through and exit said chromatography column;
   d. a sample analyte containing flow stream containing means for receiving sample analyte containing solution exiting said chromatography column; in combination with a chamber means for receiving sample analyte containing solution from said sample analyte containing flow stream containing means; said chamber means having an opening therein for entering gas and an opening therein from which a drop of sample analyte containing solution can be ejected;
   e. exit pumping means for promoting or blocking the exit of sample analyte containing solution caused to be present in said chamber means therefrom; and
   f. a means for providing a puff of gas into said opening for entering gas in said chamber means;

such that in use sample analyte containing solution from said source thereof is caused, by said entry pumping means, to enter said chromatography column, flow therethrough, exit therefrom, enter said sample analyte containing flow stream containing means and into said chamber means, with exit of said sample analyte containing solution from said chamber means being promoted, or blocked, by said exit pumping means, and such that while said sample analyte containing solution is present in said chamber means, a drop thereof can be caused to be ejected from said opening therein from which a drop of sample analyte containing solution can be ejected, by entry of a puff of gas from said means for providing a puff of gas to said opening in said chamber means for entering gas, while optionally causing said exit pumping means to block the exit of sample analyte containing solution caused to be present in said chamber means, therefrom;

2. by application of said entry pumping means causing sample analyte containing solution from said source thereof, to enter said chromatography column, flow therethrough, exit therefrom, enter said sample analyte containing flow stream containing means and into said chamber means;
3. entering a puff of gas, from said means for providing a puff of gas to said opening in said chamber means for entering gas, into said opening for entering gas in said chamber means, while optionally causing said exit pumping means to block the exit of sample analyte containing solution caused to be present in said chamber means therefrom;

to the end that a drop of sample analyte containing solution exits from said chamber means via said opening therein from which a drop of sample analyte containing solution can be ejected.

3. A method of ejecting a drop of sample analyte containing solution from a flow stream thereof as in claim 2, which further comprises the step of causing said exit pumping means to block the exit of sample analyte containing solution caused to be present in said chamber means, therefrom, simultaneous with entering a puff of gas from said means for providing a puff of gas to said opening in said chamber means for entering gas.

4. A method of ejecting a drop of sample analyte containing solution from a flow stream thereof as in claim 2, which further comprises the step of providing and positioning a receiving means under said opening in said chamber means from which a drop of sample analyte containing solution can be ejected, such that said ejected drop of sample analyte containing solution is entered into said receiving means.

5. A system for ejecting a drop of sample analyte containing solution from a flow stream thereof as in claim 1, in which said chamber means comprises a teflon tube through which has been drilled a hole essentially along a diameter thereof.

6. A system for ejecting a drop of sample analyte containing solution from a flow stream thereof as in claim 1, which further comprises a computer system for coordinated control of said entry and said exit pumping means and said means for providing a puff of gas into said opening for entering gas in said chamber means.

7. A system for ejecting a drop of sample analyte containing solution from a flow stream thereof as in claim 6, which further comprises a detection system comprising a source of a beam of electromagnetic radiation and a detector system arranged so that said beam of electromagnetic radiation is caused to pass through said sample analyte containing solution from a flow stream and such that said detector detects a change in intensity thereof when a sample analyte is near entering said chamber means, to the end that a signal is sent to said computer system.

8. A system for ejecting a drop of sample analyte containing solution from a flow stream thereof as in claim 1, in which the exit pumping means is selected from the group consisting of: (a peristaltic pump and a vacuum pump).

* * * * *